US007943034B2

(12) United States Patent
Diamond et al.

(10) Patent No.: US 7,943,034 B2
(45) Date of Patent: May 17, 2011

(54) METHOD AND APPARATUS FOR PROVIDING A STABLE VOLTAGE TO AN ANALYTICAL SYSTEM

(75) Inventors: Steven Diamond, Somerville, MA (US); Martin Forest, Nashua, NH (US); Darius Rad, Lyman, ME (US); Baoguo Wei, Salem, NH (US)

(73) Assignee: Agamatrix, Inc., Salem, NH (US)

( * ) Notice: Subject to any disclaimer, the term of this patent is extended or adjusted under 35 U.S.C. 154(b) by 880 days.

(21) Appl. No.: 11/874,777

(22) Filed: Oct. 18, 2007

(65) Prior Publication Data

US 2008/0093228 A1 Apr. 24, 2008

Related U.S. Application Data

(60) Provisional application No. 60/862,153, filed on Oct. 19, 2006.

(51) Int. Cl.
*G01N 27/327* (2006.01)
(52) U.S. Cl. .... 205/792; 205/775; 204/406; 204/403.02
(58) Field of Classification Search .......... 204/403.01–403.15, 406; 205/775, 205/777.5, 778, 792; 600/309–367; 435/4–40.52; 422/68.1–98; 436/62–71, 500–548; 403/2
See application file for complete search history.

(56) References Cited

U.S. PATENT DOCUMENTS

| | | | |
|---|---|---|---|
| 5,334,304 A | 8/1994 | Maget | |
| 5,873,990 A | 2/1999 | Wojciechowski et al. | |
| 6,366,794 B1 * | 4/2002 | Moussy et al. | 600/345 |
| 7,003,341 B2 | 2/2006 | Say et al. | |
| 7,372,277 B2 * | 5/2008 | Diamond et al. | 324/444 |
| 2006/0232278 A1 | 10/2006 | Diamond et al. | |

FOREIGN PATENT DOCUMENTS

WO 2006109273 A2 10/2006

OTHER PUBLICATIONS

Avdikos et al., "Construction and analytical applications of a palm-sized microcontroller-based amperometric analyzer", In: Sensors and Actuators B Chemical; May 27, 2005; pp. 372-378; vol. 107; Issue 1 (Abstract only).
Yun et al., "A miniaturized low-power wireless remote environmental monitoring system based on electrochemical analysis"; In: Sensors and Actuators B Chemical: Nov. 1, 2004; pp. 27-34; vol. 102; Issue 1 (Abstract only).

* cited by examiner

*Primary Examiner* — Kaj K Olsen
*Assistant Examiner* — Susan Thai
(74) *Attorney, Agent, or Firm* — Larson & Anderson, LLC

(57) ABSTRACT

A method and apparatus for provide a stable voltage to an electrochemical cell used for measurement of an analyte such as glucose in a liquid sample. The apparatus uses a circuit in which multiple switching positions provide both calibration information for use in calibration of electronic components in the circuit and error checking functionality.

15 Claims, 4 Drawing Sheets

METHOD AND APPARATUS FOR PROVIDING A STABLE VOLTAGE TO AN ANALYTICAL SYSTEM

STATEMENT OF RELATED CASES

This application claims the benefit of U.S. Provisional Application No. 60/862,153, filed Oct. 19, 2006, which application is incorporated herein by reference.

This application is related to U.S. patent application Ser. No. 10/907,806, filed Apr. 15, 2006 and PCT Application PCT/IB2006/051176, filed Apr. 14, 2006, now PCT Publication No. WO 2006/109273 A2, both of which are incorporated herein by reference.

BACKGROUND OF THE INVENTION

A number of portable, consumer devices are becoming available that make measurements of an analyte in a liquid sample such as blood or urine based upon an electrochemical measurement. A representative example of such devices is a glucose test meter, in which the user applies a small drop of blood to a test strip to obtain an indication of blood glucose level. In these devices, a single use test strip containing electrodes and reagents is inserted in a reusable meter that contains the electronics and the power supply (for example a battery) for making the measurement and displaying the results. In order to be acceptable to the consumer, the meter must be small, light-weight, and relatively inexpensive.

One of the challenges facing designers of meters of this type is providing reliable results in the face of varying conditions. It is desirable for the signal produced by the meter to be the same, regardless of the age of the battery, the ambient temperature, variability in the electronic circuits, or other loads that may be placed on the system such as when a display back lit display is in use.

SUMMARY OF THE INVENTION

The present invention provides a method and apparatus for providing a stable voltage to an electrochemical cell used for measurement of an analyte such as glucose in a liquid sample.

In accordance with one embodiment depicted in FIG. 3, the invention provides an apparatus comprising:
(a) a first connector (17) for making contact with a working electrode in an electrochemical test cell,
(b) a second connector (18) for making contact with a counter electrode in the electrochemical test cell,
(c) a working-side circuit connected to the first connector,
(d) a counter-side circuit connected to the second connector, and
(e) a microcontroller (16) receiving input from the working-side circuit and the counter-side circuit, said microcontroller being programmed to provide output of an amount of analyte in a liquid sample disposed within the electrochemical cell when the electrochemical cell is in contact with the first and second connectors,
wherein
the working-side circuit comprises
a first operational amplifier (1) having the output and inverting input connected to the first connector,
a first signal input (22, or 5,6) controllable by the microcontroller, said first signal input being connected to the non-inverting input of the first operational amplifier,
a first working-side signaling line (10 or 11) connected to the first signal input or a second working-side signaling line (11) connected between the output of the first operational amplifier and the first connector, or both; and
the counter-side circuit comprises
a voltage reference (9)
second, and third operational amplifiers (2, 3) and
first and second switches (20, 21) controllable by the microprocessor (16),
said second signal input (9) being connected to the microcontroller (16) via a first counter-side signal line (14),
said second connector (18) being connected to the microprocessor (16) via second operational amplifier (2) and a second counter-side signal line (15) when first switch 20 is closed, said second operational amplifier (2) acting as a current sensing device or current to voltage converter (I/V) with respect to the signal from the second connector, and having second signal input 9 connected to the non-inverting input,
said third operational amplifier (3 or 4) connecting the second connector (18) to the microcontroller (16) via a third counter-side signal line (12 or 13), and
said second switch (21) being disposed in a loop connecting the inverting input an the output of the second operational amplifier, whereby opening or closing the second switch (21) alters the gain of the second operational amplifier.

In accordance with another embodiment, the invention provides an analyte-detection system comprising the apparatus of the invention in combination with a test strip, disposed in contact with the connectors. The test strip is adapted for detection of a particular analyte of interest, for example glucose, and is preferably a single use disposable test strip that contains the reagents necessary for analyte detection as well as the electrodes for the electrochemical determination.

In accordance with another embodiment, the invention provides a method for providing a stable voltage to an electrochemical test cell used for electrochemical detection of an analyte in a liquid sample using the apparatus of the invention.

DETAILED DESCRIPTION OF THE INVENTION

Figure 1:
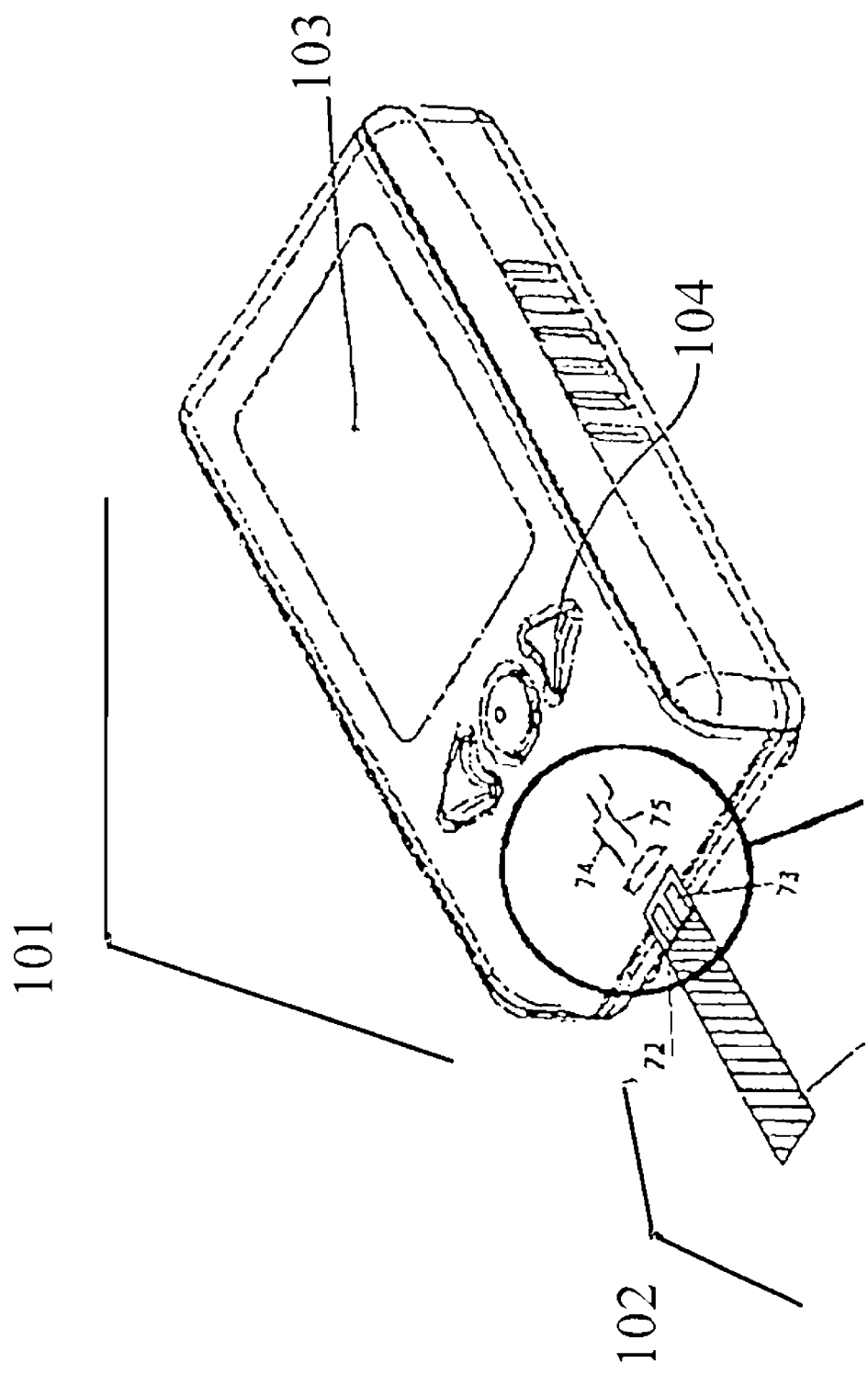
FIG. 1 shows an analyte detection system in accordance with the invention.

FIG. 1 shows an embodiment of an analyte detection system. The system comprises an apparatus or meter portion 101 and an associated test strip 102. In the apparatus shown, there are a display 103 and control buttons 104. Neither the specific configuration and appearance of the apparatus, nor the construction of the test strip are critical to the present invention. The present invention provides circuit element that are included in an analyte detection apparatus, and a method of using these circuit elements to provide improvements in analyte detection.

Figure 2:
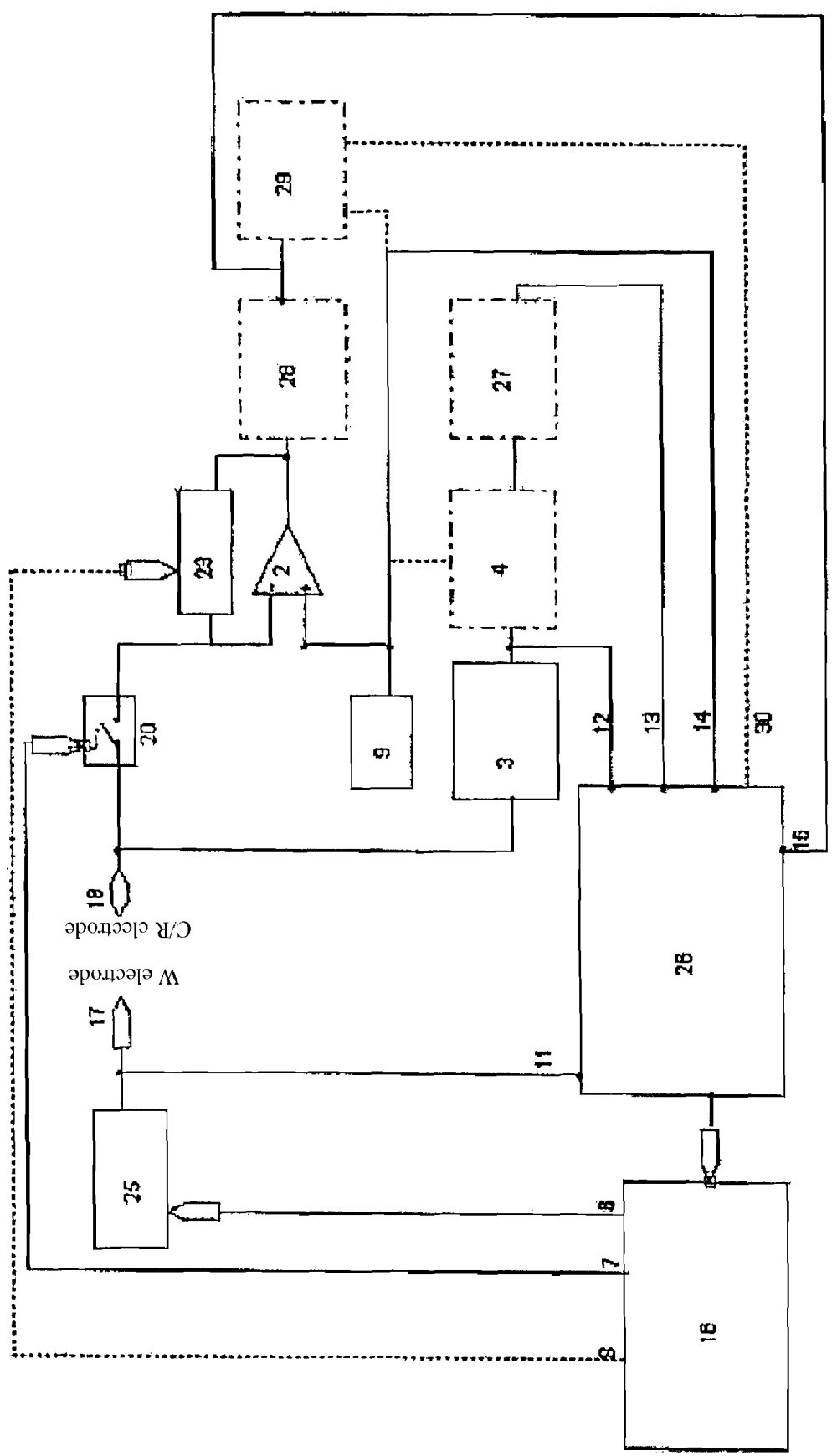
FIG. 2 shows a block diagram of a circuit for use in the apparatus of the invention.

FIG. 2 shows a block diagram of a circuit useful in the apparatus of the present invention. In this diagram, optional components are shown in dotted/dashed lines. The circuit has a connector (17) which associates with a working electrode and connector (18) which associates with a counter electrode when a test strip is connected with the apparatus. A microcontroller (16) is programmed to make a measurement and to provide output of an amount of analyte in a liquid sample disposed within the electrochemical cell when the electrochemical cell is in contact with the first and second connectors. Input signals to the microcontroller (16) are processed through an analog to digital converter (26) which may be a separate component or integrated with the microcontroller (16).

For convenience, the circuit may be viewed as having two parts, referred to herein as a working-side circuit and a counter side circuit. The labeling of these parts, however, is purely to facilitate description and does not imply anything about the actual physical arrangement of the components.

The working-side circuit comprises a input signal /control line (6) connecting the microcontroller (16) with a digital to analog converter (25) controlled by microcontroller (16) via line 6. One way to implement D/A converter (25) is to use a Filtered PWM circuit as in U.S. application Ser. No. 10/907,806. As described there, and further below, D/A converter (25) includes an isolation buffer. The working-side circuit also includes a signaling line (11) extending from between the D/A converter (25) and the connector (17) to the microcontroller (16).

The counter-side circuit comprises a current to voltage converter (I/V converter) (2), a potentiometry buffer (3), a switch 20 controlled by the microcontroller (16) via signal/control line (7), and a reference voltage (9). Switch 20 connects the connector 18 for the counter electrode to I/V converter 2, and controls the mode of operation of the circuit between amperometry and potentiometry. The reference voltage (9) sets the potential at the counter electrode (via connector 18) during amperometry. This signal can be used for the optional amperometry amplifier (29) and potentiometry amplifier (4) to increase the dynamic range of these amplifiers. The counter-side circuit also includes a sensing resistor (23) that controls the current sensitivity or gain of the I/V converter (2).

Optionally, the counter-side circuit may also include one or more of:
- a potentiometry amplifier (4) which is a gain amplifier for potential measurement used during potentiometry.
- a sensing resistor (23) that is programmable/controlled from microcontroller (16) via a signal/control line (8).
- a potentiometry Low Pass Filter (27). The potentiometry Low Pass Filter can be moved before or after the Potentiometry Amplifier (4) if present. In the case that the filter is before the amplifier (4), the signaling line (12) could be either before or after the filter.
- an amperometry Low Pass Filter (28). The Amperometry Low Pass Filter (28) can be moved before or after the Amperometry Amplifier (29), if present. In the case that the filter is before the amplifier, the signaling line (15) could be either before or after the filter.
- an amperometry amplifier (29) to provide a gain for current measured during amperometry. Provides similar functionality as having Sensing Resistor (23) be programmable.
- a signaling line (30) carrying amplified $V_{current}$, the amplified voltage representing the measured current, to the analog-to-digital converter (26).

Figure 3:
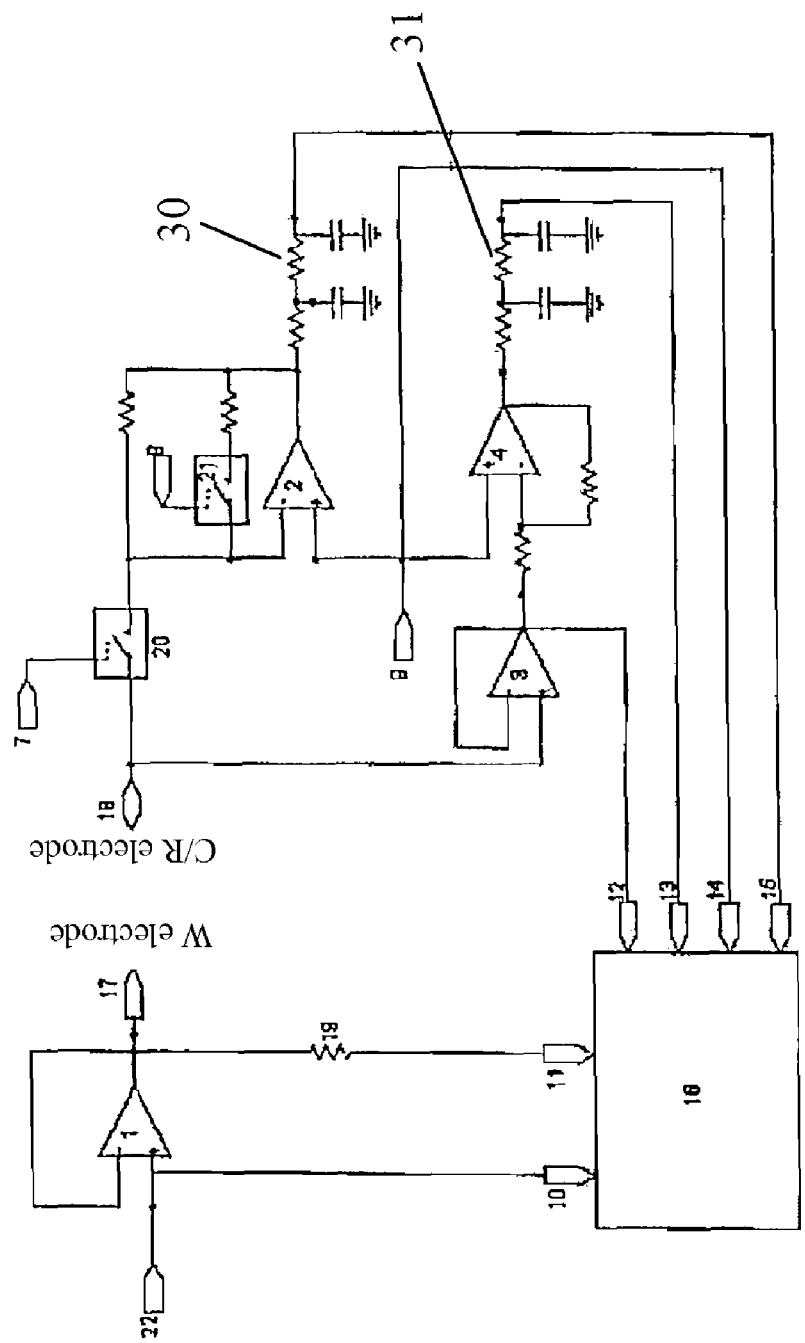
FIG. 3 shows a first embodiment of a circuit for use in the apparatus of the invention.

FIG. 3 shows a first embodiment of the circuit which is included within the apparatus of the invention. The apparatus has a first connector (17) for making contact with a working electrode in an electrochemical test cell when it is inserted in the apparatus, and a second connector (18) for making contact with a counter electrode in the electrochemical test cell. The circuit also comprises a microcontroller (16) which includes a analog to digital converter and which is connected to the first connector via a working-side circuit and the second connector via a counter-side circuit.

The working-side circuit comprises a first operational amplifier (1) having the output and inverting input connected to the first connector (17), and a signal input (22) controllable by the microcontroller. The signal input (22) is connected to the non-inverting input of the first operational amplifier (1). In this configuration, the operational amplifier acts as non-inverting unity gain amplifier, i.e., a voltage follower, and therefore acts as a buffer to provide isolation at the working electrode. In FIG. 3, there are also two working-side signaling lines (10, 11) shown. Only one of these signaling lines is necessary, but both can be present in the apparatus of the invention as shown.

In the counter-side circuit, there is a second signal input (9) which may be controllable by the microcontroller (16). The second signal input (9) is connected to the microcontroller (16) via a first counter-side signal line (14). In addition, there at least two operational amplifiers and two switches (20, 21).

In the counter-side circuit, the second connector (18) is connected to the microprocessor (16) via operational amplifier (2) and a second counter-side signal line (15) when first switch 20 is closed. Second operational amplifier (2) acts a current to voltage converter with respect to the signal from the second connector, and has second signal input 9 connected to the non-inverting input. A second switch (21) is disposed in a loop connecting the inverting input and the output of the operational amplifier (2). Opening or closing the second switch (21) alters the gain of the operational amplifier (2).

The second connector (18) is also connected to the microprocessor (16) via another pathway that includes at least one operational amplifier. FIG. 3 shows the counter-side circuit with two operational amplifiers (3, 4) in this connection, although a circuit of the invention can include only operational amplifier 3. Connector (18) is shown connected to the microprocessor via operational amplifier (3) in a non-inverting unity gain configuration via signal line (12). In FIG. 2, operational amplifier 4 acts as an inverting gain amplifier for the signal from the second connector (18) and is connected to the microcontroller (16) via signal line (13).

FIG. 3 also shows optional low pass filters 30, 31.

Figure 4:
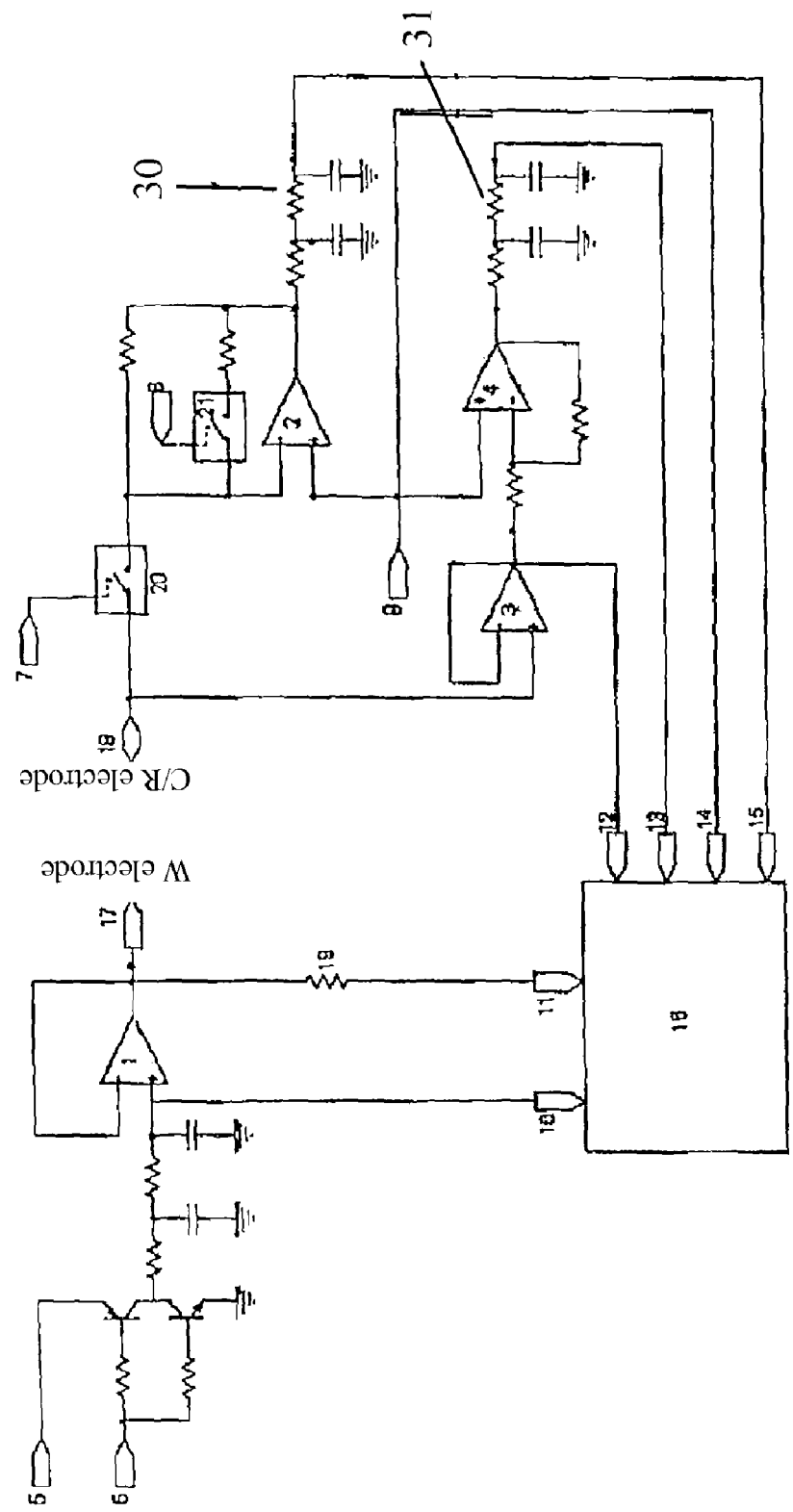
FIG. 4 shows a second embodiment of a circuit for use in the apparatus of the invention.

FIG. 4 shows an alternative embodiment of the embodiment in which the input signal 22 is a pulse-width modulated signal created from two input signals, a reference voltage input 5 and a digital input signal 6.

The method of the invention starts when the insertion of a test strip is detected, or some other condition met. This could be, for example, a start signal resulting from depression of a start button, or in the case of a continuous monitoring system a time or a time interval from a prior measurement.

The method of the invention then comprises the steps of:
(a) hardware diagnosis and calibration
(b) introduction of blood or other liquid sample to be tested for analyte into the test strip associated with the apparatus;
(c) recalibration after introduction of liquid sample
(d) perform assay for analyte.
(e) optionally perform post-assay hardware diagnosis.

The actual assay for the analyte can be performed using any electrochemical assay methods, for example amperometry, potentiometry or coulometry. Methods for assaying analytes such as glucose using all of these methods are known.

The hardware diagnosis and calibration processes involve comparing various values in the absence of sample, and after sample addition in order to adjust for variations from specification in the operational amplifiers and to diagnose fatal errors in the system of the invention. In general, the hardware diagnosis and calibration steps involve measurement of the reference, hardware diagnosis of opamp 2, and optional steps where sensing resistors are present. In the method of the invention, calibration and diagnostic measurements are performed in at least one of steps a and e and optionally e above and are performed as follows:

1) Measure the value of signal input 9 at 14.
2) Switch 20 open, switch 21 closed (low gain), measure 15. Compare to 9 as measured at 14. Value of 15 at this configuration should be closest to potential at 18 (counter electrode) during amperometry. Calculate opamp 2 offset from this. If offset is greater than a predetermined value, diagnose opamp 2 or switch 20 as damaged or out of specification.
3) Switch 20 open, switch 21 open (high gain), measure 15, compare to 9 as measured at 14 and to values from previous steps. If new values are different by some threshold from previous values, diagnose error. Because the amount of expected gain is dependent on the size of the resistor associated with operational amplifier 2, the threshold in this case is determined empirically for the particular device based on values that ale observed to correlate with incorrect glucose measurements. In addition, if these values are different by some empirically determined threshold from values measured in previous steps, diagnose error. This difference could indicate wet strip (previously used test strip) or some problem with the strip port connector, etc. Value from 15 in this position can be used in the current (I) calculation later (particularly during high gain) during amperometry as part of the analyte determination step.
4) Switch 20 closed, switch 21 closed (low gain). Measure 15, and compare to values from previous steps. If new values are different by some threshold from values measured in previous steps, diagnose error. Again, this can indicate a wet strip (previously used test strip) or some problem with the strip port connector, etc. Value from 15 in this position can be used in the current (I) calculation later (particularly during low gain). This value is the calibration of the I/V converter.
5) Switch 20 closed, switch 21 open or closed. Measure 12 and 9 and/or 15 to calculate offset of opamp 3. If offset is large, can diagnose errors in circuitry. Value of 12 can be used in the electrode potential calculation later (calculation of Working minus Reference electrodes also known as WE-RE) This is the calibration of potentiometry buffer.
6) Switch 20 closed, switch 21 open or closed. Measure 13 and 12 and/or 14 to calculate offset of opamp 4. If offset is large, can diagnose errors in circuitry. Value of 13 can be used in the electrode potential calculation later. This is calibration of the potentiometry amplifier.
7) Signals 5 & 6 with transistors, and low pass filter leading into opamp 1 are used as the equivalent of a DAC (Digital to Analog Converter) to produce a programmable variable signal. FIG. 3 is a simplified schematic of the circuit where these are replaced by another input labeled as 22, eg from a DAC to produce the same effect. Opamp 1 is still used as a buffer for this signal, but may not be necessary depending on the response time, output impedance, slew rate, current drive capacity, etc of the component(s) used to drive signal 22. While this calibration and measurement of opamp 1 may be done at any input voltage, it is preferred to do it at a voltage close to the desired voltage for the analyte measurement.
8) In the case where there is an opamp 1 in the circuit, inputs 10 and/or 11 can be measured to ultimately set the potential at 17 (W electrode) to a desired value (relative to the 18 (the C/R electrode)) via a series of successive approximations and a negative feedback program loop (as in the applications referred to above). Measuring at 11 when 19 is present may not be a good idea in a particular design and application, because depending on the circuitry driving 17 (here, opamp 1), the act of measurement may cause an instability in potential at 17 which could perturb the electrochemical cell between 17 & 18. If the electrochemical cell is perturbed, we could measure at 17 at a time where it is determined empirically that a small perturbation of the electrochemical cell is acceptable. The circuitry of each design must be tested in the context of its expected application to determine if this is an issue. Resistor 19, is present only to further illustrate that the method is valid whether the value of 17 can be measured or not. Measuring at 11 is desirable because it allows us to measure and monitor 17 more directly than if we had to measure at 10 and infer the value at 17 by a previously calculated offset, or by assuming that the offset of opamp 1 will be similar to the offset of another opamp on the same chip (eg, if opamps 1 & 3 were on the same chip (aka IC aka integrated circuit)) similarly to the related patent applications referred to above. This is calibration of the working electrode buffer.

Most errors diagnosed by the above-methods are leakage currents into opamps and switches or for the opamps and switches to be out of its specification in some other way. May also be able to diagnose strip port connector problems, strip problems, etc. The diagnostic step in 1-8 above do not all have to be performed, nor do they have to be performed in the order listed. In addition, some steps, eg, steps 6 and 8, can be carried out at the same time. All ADC inputs (10-15) can be continually monitored during all steps, or only the inputs specifically called for can be monitored/measured.

Steps 2 & 3 may not be desirable in a particular design with certain components because they may leave the inputs to opamp 3 in an indeterminate state.

Signal 9 can be produced in many ways, eg, voltage ladder between 5 & ground or from a digital to analog converter. Signal 9 can also be produced from a PWM circuit as in 5-6 in FIG. 3.

While FIGS. 2 and 3 shows opamps, resistors, capacitors, transistors, etc in the circuit as discrete components, these may be integrated into the microcontrollor or into an ASIC, etc. without departing from the scope of the invention.

Calibration of the I/V converter should be performed before the analyte detection step, and steps 2 and 3 cannot be performed during an amperometric measurement. Steps 4 and 5 cannot be performed during a potentiometric assay measurement.

What is claimed is:

1. An apparatus comprising a circuit for applying a stable voltage to an electrochemical test cell received within the apparatus, said circuit comprising:
    (a) a first connector for making contact with a working electrode in the electrochemical test cell,
    (b) a second connector for making contact with a counter electrode in the electrochemical test cell,
    (c) a working-side circuit connected to the first connector,
    (d) a counter-side circuit connected to the second connector, and
    (e) a microcontroller receiving input from the working-side circuit and the counter-side circuit, said microcontroller being programmed to provide output of an amount of analyte in a liquid sample disposed within the electrochemical cell when the electrochemical cell is in contact with the first and second connectors, wherein the working-side circuit comprises a first operational amplifier having the output and inverting input connected to the first connector, a first signal input controllable by the microcontroller, said first signal input being connected to the non-inverting input of the first operational amplifier, a first working-side signaling line connected to the first signal input or a second working-side signaling line connected between the output of the first operational amplifier and the first connector, or both; and the counter-side circuit comprises a voltage reference second, and third operational amplifiers and first and second switches controllable by the microprocessor, a second signal input being connected to the microcontroller via a first counter-side signal line, said second connector being connected to the microprocessor via second operational amplifier and a second counter-side signal line when first switch is closed, said second operational amplifier acting as a current sensing device or current to voltage converter (I/V) with respect to the signal from the second connector, and having second signal input connected to the non-inverting input, said third operational amplifier connecting the second connector to the microcontroller via a third counter-side signal line, and said second switch being disposed in a loop connecting the inverting input and the output of the second operational amplifier, whereby opening or closing the second switch alters the gain of the second operational amplifier.

2. The apparatus of claim 1, wherein the counter-side circuit further comprises a potentiometry amplifier which is a gain amplifier for potential measurement used during potentiometry.

3. The apparatus of claim 1, wherein the counter-side circuit further comprises a sensing resistor that is programmable/controlled from the microcontroller.

4. The apparatus of claim 1, wherein the counter-side circuit further comprises a potentiometry Low Pass Filter.

5. The apparatus of claim 4, wherein the counter-side circuit further comprises a potentiometry amplifier which is a gain amplifier for potential measurement used during potentiometry, and wherein the potentiometry Low Pass Filter is disposed before or after the Potentiometry Amplifier.

6. The apparatus of claim 1, wherein the counter-side circuit further comprises an amperometry amplifier to provide a gain for current measured during amperometry.

7. The apparatus of claim 1, wherein the counter-side circuit further comprises an amperometry low pass filter.

8. The apparatus of claim 7, wherein the counter-side circuit further comprises an amperometry amplifier to provide a gain for current measured during amperometry, and wherein the amperometry low pass filter is disposed before or after the amperometry amplifier.

9. The apparatus of claim 1, wherein the counter-side circuit further comprises a signaling line carrying amplified $V_{current}$ the amplified voltage representing the measured current, to the analog-to-digital converter.

10. A system for electrochemical measurement of an analyte in a liquid sample, said system comprising an apparatus and an electrochemical test cell received within the apparatus, wherein the apparatus comprises a circuit for applying a stable voltage to the electrochemical test cell, said circuit comprising:

(a) a first connector for making contact with a working electrode in the electrochemical test cell, (b) a second connector for making contact with a counter electrode in the electrochemical test cell, (c) a working-side circuit connected to the first connector, (d) a counter-side circuit connected to the second connector, and (e) a microcontroller receiving input from the working-side circuit and the counter-side circuit, said microcontroller being programmed to provide output of an amount of analyte in a liquid sample disposed within the electrochemical cell when the electrochemical cell is in contact with the first and second connectors, wherein the working-side circuit comprises a first operational amplifier having the output and inverting input connected to the first connector, a first signal input controllable by the microcontroller, said first signal input being connected to the non-inverting input of the first operational amplifier, a first working-side signaling line connected to the first signal input or a second working-side signaling line connected between the output of the first operational amplifier and the first connector, or both; and the counter-side circuit comprises a voltage reference second, and third operational amplifiers and first and second switches controllable by the microprocessor a second signal input being connected to the microcontroller via a first counter-side signal line said second connector being connected to the microprocessor via second operational amplifier and a second counter-side signal line when first switch is closed, said second operational amplifier acting as a current sensing device or current to voltage converter (I/V) with respect to the signal from the second connector, and having second signal input connected to the non-inverting input, said third operational amplifier connecting the second connector to the microcontroller via a third counter-side signal line, and said second switch being disposed in a loop connecting the inverting input and the output of the second operational amplifier, whereby opening or closing the second switch alters the gain of the second operational amplifier.

11. The system of claim 10, wherein the electrochemical test cell provides a signal indicative of the amount of glucose in a liquid sample when the stable voltage is applied by the circuit.

12. A method for providing a stable voltage to an electrochemical test cell comprising the steps of:

inserting an electrochemical test cell into an apparatus comprising a circuit for applying a stable voltage to the electrochemical test cell, performing a hardware diagnosis and calibration step on the apparatus;

introducing a liquid sample into the electrochemical test cell;

recalibrating the apparatus after introduction of the liquid sample; and performing an electrochemical assay for an analyte in the liquid sample, wherein the circuit for applying a stable voltage comprises:
(a) a first connector for making contact with a working electrode in the electrochemical test cell,
(b) a second connector for making contact with a counter electrode in the electrochemical test cell,
(c) a working-side circuit connected to the first connector,
(d) a counter-side circuit connected to the second connector, and
(e) a microcontroller receiving input from the working-side circuit and the counter-side circuit, said microcontroller being programmed to provide output of an amount of analyte in a liquid sample disposed within the electrochemical cell when the electrochemical cell is in contact with the first and second connectors, wherein the working-side circuit comprises
a first operational amplifier having the output and inverting input connected to the first connector,
a first signal input controllable by the microcontroller, said first signal input being connected to the non-inverting input of the first operational amplifier,
a first working-side signaling line connected to the first signal input or a second working-side signaling line connected between the output of the first operational amplifier and the first connector, or both; and the counter-side circuit comprises
a voltage reference
second, and third operational amplifiers and
first and second switches controllable by the microprocessor,
a second signal input being connected to the microcontroller via a first counter-side signal line,
said second connector being connected to the microprocessor via second operational amplifier and a second counter-side signal line when first switch is closed, said second operational amplifier acting as a current sensing device or current to voltage converter (I/V) with respect to the signal from the second connector, and having second signal input connected to the non-inverting input, said third operational amplifier connecting the second connector to the microcontroller via a third counter-side signal line, and said second switch being disposed in a loop connecting the inverting input and the output of the second operational amplifier, whereby opening or closing the second switch alters the gain of the second operational amplifier, and wherein the calibration step and/or the recalibration step comprises determining an offset for the second operational amplifier from a comparison of the observed reference voltage at the first counter-side signal line and the potential at the second counter signal line with the first switch open and the second switch closed, and determining the offset of the third operational amplifier from a comparison of two or more of the observed reference voltage at the first counter-side signal line, the potential at the third counter-side signal line and the potential at the second counter signal line with the first switch closed and the second switch open or closed.

13. The method of claim 12, further comprising performing one or more error checks selected from the group consisting of:

comparing the observed reference voltage at the first counter-side signal line and the potential at the second counter signal line with the first switch open and the second switch open, wherein a difference between these values greater than a predetermined threshold is indicative of an error state, and comparing an observed reference voltage at the first counter-side signal line with the first and second switches closed made prior to the application of sample with values previously measured for the reference voltage prior to the introduction of the test strip, wherein a difference in these values above a threshold level is indicative of an error state.

14. The method of claim 13, wherein the electrochemical test cell provides a signal indicative of the amount of glucose in a liquid sample when the stable voltage is applied by the circuit.

15. The method of claim 12, wherein the electrochemical test cell provides a signal indicative of the amount of glucose in a liquid sample when the stable voltage is applied by the circuit.

* * * * *